United States Patent

Gut et al.

[11] Patent Number: 5,849,665
[45] Date of Patent: Dec. 15, 1998

[54] SYNERGISTIC COMPOSITION AND PROCESS FOR SELECTIVE WEED CONTROL

[75] Inventors: Hans Gut, Lugano, Switzerland; Wolfgang Paul Iwanzik, Jakarta, Indonesia; Martin Schulte, Rheinfelden, Switzerland

[73] Assignee: Novartis Corporation, Summit, N.J.

[21] Appl. No.: 461,352

[22] Filed: Jun. 5, 1995

Related U.S. Application Data

[60] Division of Ser. No. 340,953, Nov. 17, 1994, abandoned, which is a continuation-in-part of Ser. No. 196,821, Feb. 14, 1994, abandoned, which is a continuation of Ser. No. 52,305, Apr. 23, 1993, abandoned.

[51] Int. Cl.⁶ ........................................ A01N 43/70
[52] U.S. Cl. .................................................. 504/134
[58] Field of Search ................................ 504/134

[56] References Cited

U.S. PATENT DOCUMENTS

| | | | |
|---|---|---|---|
| 4,478,635 | 10/1984 | Meyer | 71/92 |
| 4,479,821 | 10/1984 | Meyer | 71/93 |
| 4,671,819 | 6/1987 | Meyer | 71/93 |
| 4,818,273 | 4/1989 | Kleschik | 71/90 |
| 4,936,900 | 6/1990 | Hyson | 504/134 |
| 5,234,893 | 8/1993 | Hirata et al. | 504/134 |

FOREIGN PATENT DOCUMENTS

| | | |
|---|---|---|
| 0638601 | 3/1992 | Australia . |
| 1288253 | 9/1991 | Canada . |
| 0120814 | 10/1984 | European Pat. Off. . |
| 0236273 | 9/1987 | European Pat. Off. . |
| 0480871 | 4/1992 | European Pat. Off. . |

OTHER PUBLICATIONS

Brighton Crop Protection Conference 1991, pp. 31–36.
Agrochemicals Handbook, 2nd Ed. The Royal Society of Chemistry (1987), pp. A287, A1029, A1195 & A126.
Pesticide Manual 18th Ed. (1978) pp. 36–37, 63–64, 100–102, 251–796.
Pesticide Manual, 9th Ed. (1991) British Crop, pp. 619–814.

Primary Examiner—Brian M. Burn
Attorney, Agent, or Firm—Gabriel Lopez

[57] ABSTRACT

Herbicidal composition comprising
N-[2-(3,3,3-trifluoropropyl)-phenylsulfonyl]-N'-(4-methoxy-6-methyl-1,3,5-triazin-2-yl)-urea of the formula I

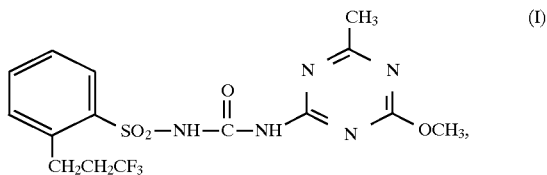

or agrochemically tolerated salts thereof, and a synergistic amount of another active substance 3,5-dibromo-4-hydroxybenzonitrile of the formula II

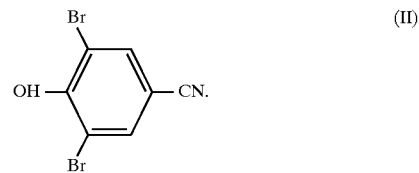

18 Claims, No Drawings

SYNERGISTIC COMPOSITION AND PROCESS FOR SELECTIVE WEED CONTROL

This is a division of Ser. No. 08/340,953, filed Nov. 17, 1994, now abandoned which is a continuation-in-part of Ser. No. 08/196,821, filed Feb. 14, 1994, now abandoned, which is a continuation of Ser. No. 08/052,305, filed Apr. 23, 1993, now abandoned.

SYNERGISTIC COMPOSITION AND PROCESS FOR SELECTIVE WEED CONTROL

The present invention relates to a synergistic composition comprising a combination of herbicidally active substances which is suitable for selective weed control in crops of useful plants, for example in crops of cereals, sorghum and rice, but in particular in crops of maize.

The invention also relates to a process and to the use of this novel composition for controlling weeds in the stated crops.

N-[2-(3,3,3-Trifluoropropyl)-phenylsulfonyl]-N'-(4-methoxy-6-methyl-1,3,5-triazin-2-yl)-urea of the formula I

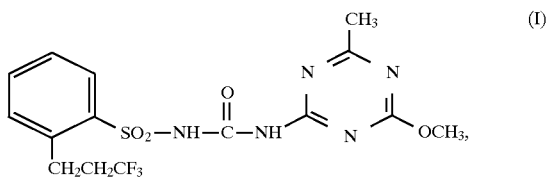

and agrochemically tolerated salts thereof have proved to be selective herbicides against weeds in crops.

The compound of the formula I and the preparation thereof are described in U.S. Pat. No. 4,671,819.

Similarly, the following compounds are known selective herbicides and some of them are commercially available:

3,5-dibromo-4-hydroxybenzonitrile (Bromoxynil), disclosed in Pesticide Manual, $8^{th}$ Ed. (1987), page 100, The British Crop Protection Council, London;

2-tert-butylamino-4-chloro-6-ethylamino-1,3,5-triazine (Terbuthylazine), disclosed in Pesticide Manual, $8^{th}$ Ed. (1987), page 778, The British Crop Protection Council, London;

N-[2-(methoxycarbonyl)-phenylsulfonyl]-N'-(4,6-bis-difluoromethoxy-pyrimidin-2-yl)-urea (Primisulfuron), disclosed in EP-B-0 084 020;

3,6-dichloro-2-methoxybenzoic acid (Dicamba), disclosed in Pesticide Manual, $8^{th}$ Ed. (1987), page 251, The British Crop Protection Council, London;

3-isopropyl-(1H)-benzo-2,1,3-thiadiazin-4-one 2,2-dioxide (Bentazone), disclosed in Pesticide Manual, $8^{th}$ Ed. (1987), page 63, The British Crop Protection Council, London;

2-chloro-4ethylamino-6-isopropylamino-1,3,5-triazine (Atrazine), disclosed in Pesticide Manual, $8^{th}$ Ed (1987), page 36, The British Crop Protection Council, London;

2-chloro-4-(1-cyano-1-methylethylamino)-6-ethylamino-1,3,5-triazine (Cyanazine), disclosed in Pesticide Manual, $8^{th}$ Ed (1987), page 198, The British Crop Protection Council, London;

2-chloro-6'-ethyl-N-(2-methoxy-1-methylethyl)acet-o-toluidide (Metolachlor), disclosed in Pesticide Manual, $8^{th}$ Ed. (1987), page 568, The British Crop Protection Council, London;

N-[3-dimethylaminocarbonyl-2-pyridylsulfonyl]-N'-(4,6-dimethoxypyrimidin-2-yl)urea (Nicosulfuron), disclosed in The Agrochemicals Handbook, $2^{nd}$ Ed., The Royal Society of Chemistry 1987;

Methyl 3-(4-methoxy-6-methyl-1,3,5-triazin-2-yl-carbamoylsulfamoyl)thiophene-2-carboxylate (Thifensulfuron-methyl), disclosed in Pesticide Manual, $9^{th}$ Ed. (1991), page 814, The British Crop Protection Council, London;

6-chloro-3-phenylpyridazin-4-yl S-octylthiocarbonate (Pyridate), disclosed in Pesticide Manual, $8^{th}$ Ed. (1987), page 731, The British Crop Protection Council, London;

N-[2-(2-chloroethoxy)-phenylsulfonyl]-N'-(4-methoxy-6methyl-1,3,5-triazin-2-yl)urea (Triasulfuron), disclosed in The Agrochemicals Handbook, $2^{nd}$ Ed., The Royal Society of Chemistry 1987;

(RS)-2-(4-chloro-o-tolyloxy)-propionic acid (MCPP, Mecoprop), disclosed in Pesticide Manual, $8^{th}$ Ed. (1987), page 522, The British Crop Protection Council, London;

N-[2-(2-methoxyethoxy)-phenylsulfonyl]-N'-(4,6-dimethoxy-1,3,5-triazin-2-yl)-urea (Cinosulfuron), disclosed in U.S. Pat. No. 4,479,821;

N-[2-(methoxycarbonyl)-phenylsulfonyl]-N'-(4,6dimethoxy-pyrimidin-2-yl)-urea (Bensulfuron-methyl), disclosed in The Agrochemicals Handbook, $2^{nd}$ Ed., The Royal Society of Chemistry 1987;

3,7-dichloro-8-quinolinecarboxylic acid (Quinclorac), disclosed in The Agrochemicals Handbook, $2^{nd}$ Ed., The Royal Society of Chemistry 1987;

2-chloro-2',6'-diethyl-N-(2-propoxyethyl)-acetanilide (Pretilachlor), disclosed in Pesticide Manual, $8^{th}$ Ed. (1987), page 689, The British Crop Protection Council, London;

S-4-chlorobenzyl diethyl(thiocarbamate) (Thiobencarb), disclosed in Pesticide Manual, $8^{th}$ Ed. (1987), page 796, The British Crop Protection Council, London;

(RS)-2-bromo-3,3-dimethyl-N-(1-methyl-1-phenylethyl)-butyramide (Bromobutide), disclosed in The Agrochemicals Handbook, $2^{nd}$ Ed., The Royal Society of Chemistry 1987;

2-(1,3-benzothiazol-2-yloxy)-N-methylacetanilide (Mefenacet), disclosed in Pesticide Manual, $8^{th}$ Ed (1987), page 526, The British Crop Protection Council, London;

S-ethyl N,N-hexamethylenethiocarbamate (Molinate), disclosed in Pesticide Manual, $8^{th}$ Ed. (1987),page 578, The British Crop Protection Council, London;

3-chloro-5-(4',6'-dimethoxypyrimidin-2'-ylcarbamoylsulfamoyl)-1-methylpyrazole-4-methylcarboxylate (NC-319), disclosed in Proceedings of the Brighton Crop-Protection Conference, Vol. 1, 1991, p. 31;

5,7-dimethoxy-N-[2,6-dichloro-3-methyl-phenyl]-1,2,4-triazolo[1,5-a]pyrimidine-2-sulfonamide (DE-511), disclosed in U.S. Pat. No. 4,818,273 (Example No. 89).

It has now been found that the compound of the formula I can be combined in an advantageous manner with at least one of the herbicidally active compounds disclosed in the abovementioned publications. Such combinations each have a synergistic (superadditive) herbicidal effect over and above the purely additive effect of the respective compounds at a given application rate.

The present invention therefore proposes a novel synergistic composition for selective weed control comprising, as an active substance, on the one hand N-[2-(3,3,3-trifluoropropyl)-phenylsulfonyl]-N'-(4-methoxy-6-methyl-1,3,5-triazin-2-yl)-urea of the formula I

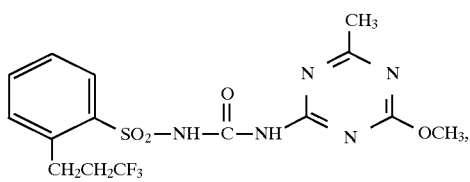 (I)

or the agrochemically tolerated salts thereof and, on the other hand, a synergistically active amount either of the active substance 3,5-dibromo-4-hydroxybenzonitrile of the formula II

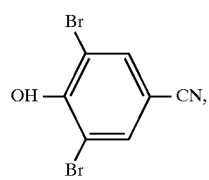 (II)

and/or of the active substance 2-tert-butylamino-4-chloro-6-ethylamino-1,3,5-triazine of the formula III

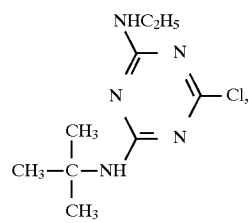 (III)

and/or of the active substance N-[2-(methoxycarbonyl)-phenylsulfonyl]-N'-(4,6-bis-difluoromethoxypyrimidin-2-yl)-urea of the formula IV

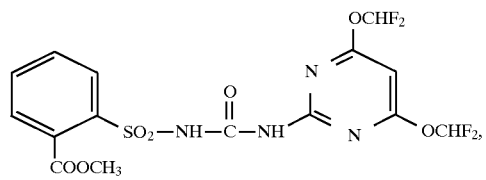 (IV)

and/or of the active substance 3,6-dichloro-2-methoxybenzoic acid of the formula V

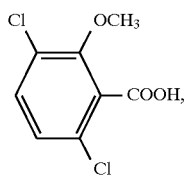 (V)

and/or of the active substance 3-isopropyl-(1H)-benzo-2,1,3-thiadiazin-4-one 2,2-dioxide of the formula VI

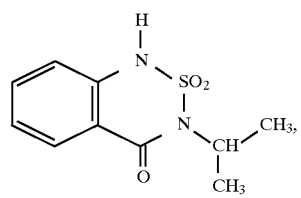 (VI)

and/or of the active substance 2-chloro-4-ethylamino-6-isopropylamino-1,3,5-triazine of the formula VII

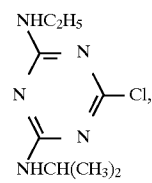 (VII)

and/or of the active substance 2-chloro-4-(1-cyano-1-methylethylamino)-6-ethylamino-1,3,5-triazine of the formula VIII

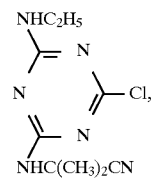 (VIII)

and/or of the active substance 2-chloro-6'-ethyl-N-(2-methoxy-1-methylethyl)acet-o-toluidide of the formula IX

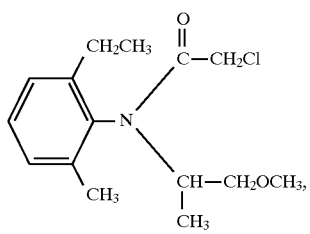 (IX)

and/or of the active substance N-[3-dimethylaminocarbonyl-2-pyridylsulfonyl]-N'-(4,6-dimethoxypyrimidin-2-yl)-urea of the formula X

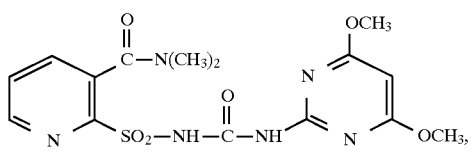 (X)

and/or of the active substance N-[2-(methoxycarbonyl)-3-thiophenylsulfonyl]-N'-(4-methyl-6-methoxy-1,3,5-triazin-2-yl)-urea of the formula XI

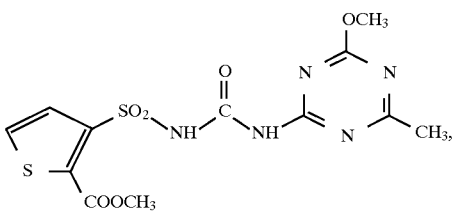 (XI)

and/or of the active substance 6-chloro-3-phenylpyridazin4-yl S-octylthiocarbonate of the formula XII

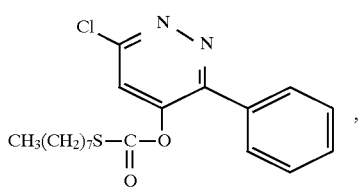 (XII)

and/or of the active substance N-[2-(2-chloroethoxy)-phenylsulfonyl]-N'-(4-methoxy-6-methyl-1,3,5-triazin-2-yl)-urea of the formula XIII

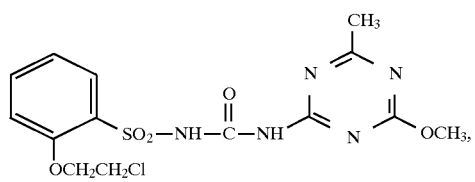

and/or of the active substance (RS)-2-(4-chloro-o-tolyloxy)-propionic acid of the formula XIV

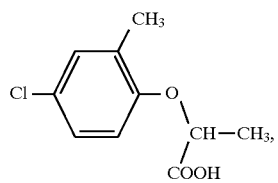

and/or of the active substance N-[2-(2-methoxyethoxy)-phenylsulfonyl]-N'-(4,6-dimethoxy-1,3,5-triazin-2-yl)-urea of the formula XV

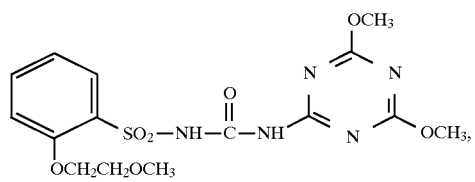

and/or of the active substance N-[2-(methoxycarbonyl)-phenylsulfonyl]-N'-(4,6-dimethoxy-pyrimidin-2-yl)-urea of the formula XVI

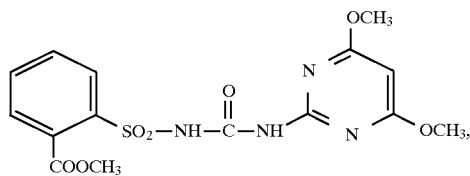

and/or of the active substance 3,7-dichloro-8-quinolinecarboxylic acid of the formula XVII

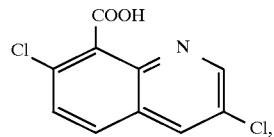

and/or of the active substance 2-chloro-2',6'-diethyl-N-(2-propoxyethyl)-acetanilide of the formula XVIII

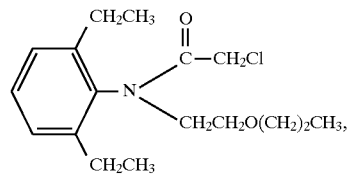

and/or of the active substance S-4-chlorobenzyl diethylthiocarbamate of the formula XIX

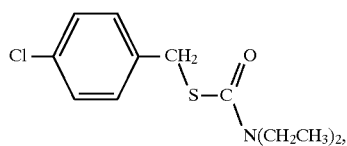

and/or of the active substance (RS)-2-bromo-3,3-dimethyl-N-(1-methyl-1-phenyl-ethyl)-butyramide of the formula XX

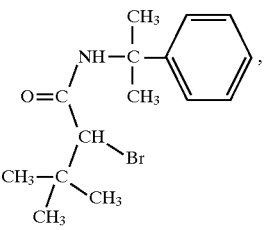

and/or of the active substance 2-(1,3-benzothiazol-2-yloxy)-N-methylacetanilide of the formula XXI

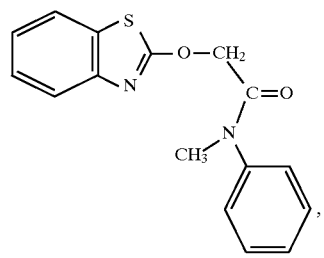

and/or of the active substance S-ethyl N,N-hexamethylenethiocarbamate of the formula XXII

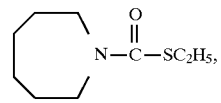

and/or of the active substance of the formula XXIII

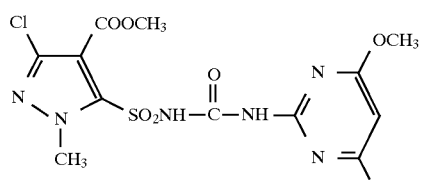

and/or of the active subtance of the formula XXIV

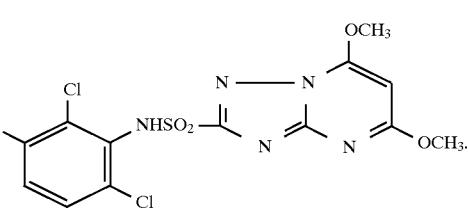

It is very surprising that the combination of the active substance of the formula I with at least one of the active substances of the formulae II, III, IV, V, VI, VII, VIII, IX, X, XI, XII, XIII, XIV, XV, XVI, XVII, XVIII, XIX, XX, XXI, XXII, XXIII or XXIV not only causes an additive enhancement of the action spectrum with respect to the weeds to be controlled, which in principle was to be expected, but achieves a synergistic effect which extends the activity limits of both the products from two aspects:

On the one hand, the application rates of the individual compounds I and II to XXIV can be reduced while achieving a constant good effect. On the other hand, the inventive mixture achieves a high degree of weed control even where the individual compounds of the mixture have become completely ineffective in the region of very low application rates. This results in a substantial broadening of the weed spectrum and an additional increase in the safety margin with regard to the crops, as is necessary and desired in the case of an unintentional overdose of active substance. The inventive mixtures, especially the mixture of the compound of formula I with the compound of formula IV, allow for greater rotational flexibility while still providing outstanding weed control in crops, especially in corn.

The herbicide mixture according to the invention can advantageously be used in a large number of agronomically important weeds, for example Chenopodium, Polygonum, Solanum, Amaranthus, Lamium, Echinochloa, Sagittaria, Ipomoea and Cyperus, in crops, pre-emergent, in the irrigation water (transplanted rice) and in particular post-emergent.

Corresponding herbicide mixtures according to the invention can advantageously be used for weed control in the following crops: cereals (wheat, barley, rye, millet and oats), sorghum, rice and in particular maize.

The mixture of the compounds of the formulae I and II to XXIV has a synergistic, selective herbicidal action in each case in a wide mixing range.

The active substance combination according to the invention contains an active substance of the formula I and at least one of the active substances of the formulae I to XXIV in any ratio, as a rule with an excess of one component over the others. Preferred ratios for the mixture of the active substance of the formula I and at least one of the mixing partners of the formulae II to XXIV are between 1:0.05 and 1:200 and in particular between 1:0.1 and 1:125.

Herbicidal compositions which contain, as active substance, on the one hand the compound of the formula I and on the other hand a synergistic amount of at least one of the active substances of the formulae II to XXII, XXIII or XXIV are preferred.

Combinations of the compound of the formula I with the compounds of the formulae II, III, IV, XXIII or XXIV have proved very particularly effective synergistic active substance mixtures.

Herbicidal compositions which contain, as active substance, on the one hand the compound of the formula I and on the other hand a synergistic amount of at least one of the active substances of the formula XIII, XIV or XXIV are also preferred.

Herbicidal compositions which contain, as active substance, on the one hand the compound of the formula I and on the other hand a synergistic amount of at least one of the active substances of the formulae XV to XXIII are likewise preferred.

Mixtures which contain one or two active substances of the formulae II, III, IV, V, VI, VII, VIII, IX, X, XI, XII, XIII, XIV, XV, XVI, XVII, XVIII, XIX, XX, XXI, XXII, XXIII or XXIV in addition to the compound of the formula I are of particular importance.

The application rate can be varied within wide ranges and depends on the characteristics of the soil, the method of application (pre-emergent or post-emergent; seed dressing; application in the seed furrow; no tillage application etc), the crop, the weed to be controlled, the prevailing climatic conditions and other factors determined by the method of application, time of application and target crop. In general, the active substance mixture according to the invention can be applied at a rate of 10 to 2000 g of active substance/ha, in particular 20 to 1000 g of active substance/ha.

The herbicidal composition according to the invention which contains a compound of the formula I and a synergistic amount of at least one of the active substances of the formulae II to XII, XXIII and/or XXIV, in particular of the formulae II to IV, XXIII and/or XXIV, can advantageously be used for selective weed control in maize.

The herbicidal composition according to the invention which contains a compound of the formula I and a synergistic amount of at least one of the active substances of the formula XIII, XIV or XXIV can advantageously be used for selective weed control in cereals.

The herbicidal composition according to the invention which contains a compound of the formula I and a synergistic amount of at least one of the active substances of the formulae XV to XXIII can advantageously be used for selective weed control in rice.

The mixtures of the compound of the formula I with the compounds of the formulae II to XXIV are used in unchanged form, as obtainable from synthesis, or preferably with the assistants customary in the art of formulation and are therefore processed to give, for example, emulsifiable concentrates, directly sprayable or dilutable solutions, dilute emulsions, wettable powders, soluble powders, dusts, granules or encapsulations in, for example, polymeric substances in a known manner. The application methods, such as spraying, atomising, dusting, wetting, scattering or pouring, are chosen, as in the case of the type of composition, according to the objectives and the prevailing conditions.

The formulations, i.e. the compositions or preparations containing the active substances of the formulae I and II to XXIV and, if desired, one or more solid or liquid adjuvants are prepared in a known manner, for example by thoroughly mixing and/or milling the active substances with extenders, for example with solvents, solid carriers and, if desired, surface-active compounds (surfactants).

Suitable solvents are aromatic hydrocarbons, in particular the $C_8$ to $C_{12}$ fractions, such as mixtures of alkylbenzenes, e.g. xylene mixtures or alkylated naphthalenes; aliphatic and cycloaliphatic hydrocarbons, such as paraffins, cyclohexane or tetrahydronaphthalene; alcohols, such as ethanol, propanol or butanol; glycols and ethers and esters thereof, such as propylene glycol or dipropylene glycol ether, ketones, such as cyclohexanone, isophorone or diacetone alcohol, strongly polar solvents, such as N-methyl-2-pyrrolidone, dimethyl sulfoxide or water, vegetable oils and esters thereof, such as rapeseed oil, castor oil or soybean oil, and, if desired, also silicone oils.

As a rule, crushed natural minerals, such as calcite, talc, kaolin, montmorillonite or attapulgite, are used as solid carriers, for example for dusts and dispersible powders. Finely divided silica or finely divided absorptive polymers can also be added in order to improve the physical properties. Porous types, for example pumice, brick fragments, sepiolite or bentonite, are suitable particulate, adsorptive carriers for granules, and, for example, calcite or sand are suitable non-sorptive carriers. A large number of pregranulated inorganic or organic materials, in particular dolomite or comminuted plant residues, can also be used.

Nonionic, cationic and/or anionic surfactants having good emulsifying, dispersing and wetting properties are suitable surface-active compounds, depending on the type of active substances of the formulae I and II to XXIV to be formulated. Surfactants are also understood as meaning surfactant mixtures.

Suitable anionic surfactants may be both so-called water-soluble soaps and water-soluble synthetic surface-active compounds.

Soaps are the alkali metal, alkaline earth metal or substituted or unsubstituted ammonium salts of higher fatty acids ($C_{10}$–$C_{22}$), for example the sodium or potassium salts of oleic or stearic acid, or of natural fatty acid mixtures which can be obtained, for example, from coconut oil or tallow oil. The salts of fatty acids and methyltaurine may also be mentioned.

However, so-called synthetic surfactants, in particular fatty alcoholsulfonates, fatty alcohol sulfates, sulfonated benzimidazole derivatives or alkylarylsulfonates, are more frequently used.

The fatty alcohol sulfonates or sulfates are as a rule in the form of alkali metal, alkaline earth metal or unsubstituted or substituted ammonium salts and possess an alkyl radical having 8 to 22 C atoms, alkyl also including the alkyl moiety of acyl radicals, for example the sodium or calcium salt of ligninsulfonic acid, of the dodecylsulfuric ester or of a fatty alcohol sulfate mixture prepared from natural fatty acids. These also include the salts of the sulfuric esters and sulfonic acids of fatty alcohol/ethylene oxide adducts. The sulfonated benzimidazole derivatives preferably contain 2 sulfonic acid groups and a fatty acid radical having 8–22 C atoms. Alkylarylsulfonates are, for example, the sodium, calcium or triethanolamine salts of dodecylbenzenesulfonic acid, of dibutylnaphthalenesulfonic acid or of a naphthalenesulfonic acid/formaldehyde condensate.

Corresponding phosphates, for example salts of the phosphoric ester of a p-nonylphenol-(4–14)-ethylene oxide adduct or phospholipids are also suitable.

Suitable nonionic surfactants are primarily polyglycol ether derivatives of aliphatic or cycloaliphatic alcohols, saturated or unsaturated fatty acids and alkylphenols, which may contain 3 to 30 glycol ether groups and 8 to 20 carbon atoms in the (aliphatic) hydrocarbon radical and 6 to 18 carbon atoms in the alkyl radical of the alkylphenols.

Further suitable nonionic surfactants are the water-soluble polyethylene oxide adducts with polypropylene glycol, ethylenediaminopolypropylene glycol and alkylpolypropylene glycol having 1 to 10 carbon atoms in the alkyl chain, which adducts contain 20 to 250 ethylene glycol ether groups and 10 to 100 propylene glycol ether groups. The stated compounds usually contain 1 to 5 ethylene glycol units per propylene glycol unit.

Examples of nonionic surfactants are nonylphenol polyethoxyethanols, castor oil polyglycol ether, polypropylene/polyethylene oxide adducts, tributylphenoxypolyethoxyethanol, polyethylene glycol and octylphenoxypolyethoxyethanol.

Fatty esters of polyoxyethylene sorbitan, such as polyoxyethylenesorbitan trioleate, are also suitable.

The cationic surfactants are in particular quaternary ammonium salts which contain, as N substituents, at least one alkyl radical having 8 to 22 C atoms and, as further substituents, lower alkyl, benzyl or lower hydroxyalkyl radicals, each of which may be halogenated. The salts are preferably in the form of halides, methylsulfates or ethylsulfates, for example stearyltrimethylammonium chloride or benzyldi-(2-chloroethyl)-ethylammonium bromide.

The surfactants customary in the art of formulation, which may also be used in the compositions according to the invention, are described, inter alia, in the following publications:

—"Mc Cutcheon's Detergents and Emulsifiers Annual", Mc Publishing Corp., Glen Rock, N.J., 1988.

—M. and J. Ash, "Encyclopedia of Surfactants", Vol. I–III, Chemical Publishing Co., New York, 1980–1981.

—Dr. Helmut Stache "Tensid-Taschenbuch", Carl Hanser Verlag, Munich/Vienna 1981.

The herbicidal preparations contain, as a rule, 0.1 to 99%, in particular 0.1 to 95%, of active substance mixture comprising the compound of the formula I with the compounds of the formulae II to XXIV, 1 to 99% of a solid or liquid adjuvant and 0 to 25%, in particular 0.1 to 25%, of a surfactant.

While concentrated compositions are preferred as commercial products, the end user generally uses dilute compositions.

The compositions can also contain further adjuvants, such as stabilisers, for example vegetable oils which may be epoxidised (epoxidised coconut oil, rapeseed oil or soybean oil), antifoams, for example silicone oil, preservatives, viscosity regulators, binders, tackifiers and fertilisers or other active substances for achieving special effects.

Preferred formulations have in particular the following compositions: (%=percent by weight)

Emulsifiable concentrates:
  Active substance mixture: 1 to 90%, preferably 5 to 20%
  Surfactant: 1 to 30%, preferably 10 to 20%
  Liquid carrier: 5 to 94%, preferably 70 to 85%

Dusts:
  Active substance mixture: 0.1 to 10%, preferably 0.1 to 1%
  Solid carrier: 99.9 to 90%, preferably 99.9 to 99%

Suspension concentrates:
  Active substance mixture: 5 to 75%, preferably 10 to 50%
  Water: 94 to 24%, preferably 88 to 30%
  Surfactant: 1 to 40%, preferably 2 to 30%

Wettable powders:
  Active substance mixture: 0.5 to 90%, preferably 1 to 80%
  Surfactant: 0.5 to 20%, preferably 1 to 15%
  Solid carrier: 5 to 95%, preferably 15 to 90%

Granules:
  Active substance mixture: 0.5 to 30%, preferably 3 to 15%
  Solid carrier: 99.5 to 70%, preferably 97 to 85%

The examples which follow illustrate the invention further without restricting it.

1. FORMULATION EXAMPLES

Mixtures of the compounds of the formulae I and II to XXIV (%=percent by weight)

| F1. Wettable powder | a) | b) | c) | d) |
|---|---|---|---|---|
| Mixture of active substance of the formula I with at least one of the active substances of the formulae II to XXIV | 10% | 20% | 5% | 30% |
| Sodium ligninsulfonate | 5% | 5% | 5% | 5% |
| Sodium lauryl sulfate | 3% | — | 3% | — |
| Sodium diisobutylnaphthalenesulfonate | — | 6% | — | 6% |
| Octylphenol polyethylene glycol ether (7–8 mol of EO) | — | 2% | — | 2% |
| Finely divided silica | 5% | 27% | 5% | 27% |
| Kaolin | 67% | — | 67% | — |

The active substance mixture is mixed well with the adjuvants and thoroughly milled in a suitable mill. Wettable powders which can be diluted with water to give suspensions of any desired concentration are obtained.

| F2. Emulsion concentrate | a) | b) | c) |
|---|---|---|---|
| Mixture of active substance of the formula I with at least one of the active substances of the formulae II to XXIV | 5% | 5% | 12% |
| Octylphenol polyethylene glycol ether (4–5 mol of EO) | 3% | 3% | 3% |
| Calcium dodecylbenzenesulfonate | 3% | 3% | 2% |
| Castor oil polyglycol ether (36 mol of EO) | 4% | 4% | 4% |
| Cyclohexanone | 30% | 30% | 31% |
| Xylene mixture | 50% | 35% | 35% |

Emulsions of any desired concentration can be prepared from these concentrates by dilution with water.

| F3. Dusts | a) | b) | c) | d) |
|---|---|---|---|---|
| Mixture of active substance of the formula I with at least one of the active substances of the formulae II to XXIV | 2% | 2% | 2% | 4% |
| Talc | 3% | 4% | 4% | 8% |
| Kaolin | 95% | 92% | 94% | 88% |

Ready-to-use dusts are obtained by mixing the active substance mixture with the carrier and milling the mixture in a suitable mill.

| F4. Extruder granules | a) | b) | c) |
|---|---|---|---|
| Mixture of active substance of the formula I with at least one of the active substances of the formulae II to XXIV | 5% | 3% | 5% |
| Sodium ligninsulfonate | 2% | 2% | 2% |
| Carboxymethylcellulose | 1% | 1% | 1% |
| Kaolin | 87% | 87% | 77% |

The active substance mixture is mixed with the adjuvants, milled, and moistened with water. This mixture is extruded and then dried in an air current.

| F5. Coated granules | a) | b) |
|---|---|---|
| Mixture of active substance of the formula I with at least one of the active substances of the formulae II to XXIV | 1.5% | 3% |
| Polyethylene glycol (MW 200) | 3% | 3% |
| Kaolin | 94% | 89% |

The finely milled active substance mixture is uniformly applied, in a mixer, to the kaolin moistened with polyethylene glycol. Dust-free coated granules are obtained in this manner.

| F6. Suspension concentrate | a) | b) |
|---|---|---|
| Mixture of active substance of the formula I with at least one of the active substances of the formulae II to XXIV | 20% | 20% |
| Ethylene glycol | 10% | 10% |
| Nonylphenol polyethylene glycol ether (15 mol of EO) | 6% | 6% |
| Sodium ligninsulfonate | 10% | 10% |
| Carboxymethylcellulose | 1% | 1% |
| 37% aqueous formaldehyde solution | 0.2% | 0.2% |
| Silicone oil in the form of a 75% aqueous emulsion | 0.8% | 0.8% |
| Water | 32% | 12% |

The finely milled active substance mixture is thoroughly mixed with the adjuvants. A suspension concentrate from which suspensions of any desired concentration can be prepared by dilution with water are obtained in this manner.

It is often more practical to formulate the active substance of the formula I and the mixing partners of the formulae II to XXIV individually and then to combine them in the desired ratio as a tank mix in water shortly before application in the applicator.

2. BIOLOGICAL EXAMPLES

A synergistic effect is present whenever the action of the active substance combination comprising the compound of the formula I and at least one of the compounds of the formulae II to XXIV is greater than the sum of the actions of the individual active substances applied.

The expected herbicidal action Ae for a given combination of at least two herbicides can be calculated as follows (cf. COLBY, S. R., "Calculating synergistic and antagonistic response of herbicide combinations", Weeds 15, pages 20–22, 1967):

$$Ae = X + \frac{Y \cdot (100 - X)}{100}$$

X=Percent inhibition of growth on treatment with the compound of the formula I at an application rate of p kg per hectare in comparison with the untreated control (=0%).

Y=Percent herbicidal action on treatment with at least one compound of the formulae II to XXIV at an application rate of q kg per hectare in comparison with the untreated control.

Ae=Expected herbicidal action (percent inhibition of growth in comparison with the untreated control) after treatment with the compounds of the formulae I and II to XXIV at an application rate of p+q kg of active substance per hectare.

If the action actually observed is greater than the expected value Ae, a synergistic effect is present.

The synergistic effect of the combinations of the active substance of the formula I with the active substances of the formulae II to XXIV is demonstrated in the following examples.

Example B1

Description of Test for Postemergent Application

The seeds of the test plants are sown in plastic pots, which contain 0.5 l of sterilised field soil, in a greenhouse. After emergence, the plants are sprayed with an aqueous dispersion of the active substance combination when they have developed 2 or 3 leaves. The application rate of active substance is adjusted by suitable dilution of the concentrate. 55 ml of dispersion, prepared from an emulsion concentrate (Example F2), are sprayed per m$^2$. The test plants are further cultivated in the greenhouse and watered daily.

After 3 weeks, the herbicidal action is rated in comparison with an untreated control group. The percentage inhibition of growth in comparison with the untreated control is recorded. The following linear scale is used as a basis:
100%=plants dead
50%=average action
0%=like untreated control Example B2

Synergistic Herbicidal Action for Paddy

The test plants are sown in, or transplanted into, plastic troughs which contain moist sterilised field soil. Three days after sowing, the water level is raised above the level of the soil surface (2 cm) and the active substances are applied into the accumulated water. The application rate of the active substances is adjusted by suitable dilution of the concentrate, prepared from an emulsion concentrate (Example F2), with water. The test plants are further cultivated in the greenhouse with daily watering and under optimum growth conditions, i.e. at 25°–30° C.

After 3 weeks, the herbicidal action is rated in comparison with an untreated control group. The percentage reduction of the biomass in comparison with the untreated control is recorded. The following linear scale is used as a basis:
100%=plants dead
50%=average action
0%=like untreated control The results of the comparison are recorded in Tables 1, 2 and 3, together with the expected values Ae calculated using the Colby formula. The formula numbers of the particular active substances used, the application rates thereof [g of active substance/ha] and the weeds tested are shown.

The tables relate specifically to the following:

Table 1: Tests in maize with Chenopodium polyspermum, Polygonum convolvulus, Amaranthus retroflexus, Solanum nigrum and Ipomoea purpurea by the postemergence method;

Table 2: Tests in cereals with Chenopodium album and Lamium purpureum by the postemergence method;

Table 3: Tests in rice with Echinochloa crus-galli, Sagittaria pygmaea and Cyperus serotinus by application in the irrigation water (transplanted rice).

TABLE 1

| Comp. No. | Application rate [g of active substance/ha] | Weed: Chenopodium polyspermum [%] | Ae [expected value] |
|---|---|---|---|
| I | 10 | 0 | |
| V | 120 | 55 | |
| I + V | 10 + 120 | 100 | 55 |
| I | 20 | 50 | |
| IX | 1000 | 0 | |
| I + IX | 20 + 1000 | 90 | 50 |

| Comp. No. | Application rate [g of active substance/ha] | Weed: Polygonum convolvulus [%] | Ae [expected value] |
|---|---|---|---|
| I | 10 | 30 | |
| II | 125 | 0 | |
| I + II | 10 + 125 | 100 | 30 |
| I | 5 | 0 | |
| VIII | 250 | 0 | |
| I + VIII | 5 + 250 | 100 | 0 |
| I | 5 | 0 | |
| VII | 250 | 0 | |
| I + VII | 5 + 250 | 99 | 0 |
| I | 10 | 30 | |
| IV | 4 | 0 | |
| I + IV | 10 + 4 | 95 | 30 |

| Comp. No. | Application rate [g of active substance/ha] | Weed: Amaranthus retroflexus [%] | Ae [expected value] |
|---|---|---|---|
| I | 10 | 30 | |
| XII | 500 | 70 | |
| I + XII | 10 + 500 | 85 | 79 |
| I | 10 | 30 | |
| X | 15 | 0 | |
| I + X | 10 + 15 | 85 | 30 |
| I | 10 | 30 | |
| XI | 5 | 0 | |
| I + XI | 10 + 5 | 85 | 30 |
| I | 5 | 0 | |

TABLE 1-continued

| VI | 500 | 0 | |
|---|---|---|---|
| I + VI | 5 + 500 | 85 | 0 |

| Comp. No. | Application rate [g of active substance/ha] | Weed: Solanum nigrum [%] | Ae [expected value] |
|---|---|---|---|
| I | 10 | 0 | |
| III | 250 | 0 | |
| I + III | 10 + 250 | 98 | 0 |

| Comp. No. | Application rate [g of active substance/ha] | Weed: Ipomoea purpurea [%] | Ae [expected value] |
|---|---|---|---|
| I | 20 | 65 | |
| X | 15 | 0 | |
| I + X | 20 + 15 | 85 | 65 |

TABLE 2

| Comp. No. | Application rate [g of active substance/ha] | Weed: Chenopodium album [%] | Ae [expected value] |
|---|---|---|---|
| I | 2.5 | 75 | |
| XIII | 2.5 | 0 | |
| I + XIII | 2.5 + 2.5 | 85 | 75 |

| Comp. No. | Application rate [g of active substance/ha] | Weed: Lamium purpureum [%] | Ae [expected value] |
|---|---|---|---|
| I | 2, 5 | 55 | |
| XIV | 125 | 0 | |
| I + XIV | 2, 5 + 125 | 80 | 55 |

TABLE 3

| Comp. No. | Application rate [g of active substance/ha] | Weed: Echinochloa crus-galli [%] | Ae [expected value] |
|---|---|---|---|
| I | 8 | 0 | |
| XIX | 500 | 60 | |
| I + XIX | 8 + 500 | 97 | 60 |
| I | 15 | 25 | |
| XXI | 125 | 75 | |
| I + XXI | 15 + 125 | 99 | 81 |
| I | 8 | 0 | |
| XVIII | 60 | 80 | |
| I + XVIII | 8 + 60 | 90 | 80 |
| I | 15 | 25 | |
| XVII | 60 | 70 | |
| I + XVII | 15 + 60 | 95 | 78 |

| Comp. No. | Application rate [g of active substance/ha] | Weed: Sagittaria pygmaea [%] | Ae [expected value] |
|---|---|---|---|
| I | 8 | 89 | |
| XXII | 125 | 0 | |
| I + XXII | 8 + 125 | 98 | 89 |
| I | 8 | 89 | |
| XV | 4 | 35 | |
| I + XV | 8 + 4 | 97 | 93 |

| Comp. No. | Application rate [g of active substance/ha] | Weed: Cyperus serotinus [%] | Ae [expected value] |
|---|---|---|---|
| I | 30 | 50 | |
| XVI | 4 | 35 | |
| I + XVI | 30 + 4 | 95 | 68 |

TABLE 3-continued

| I     | 8        | 27 |
|-------|----------|----|
| XX    | 1000     | 0  |
| I + XX| 8 + 1000 | 97 | 27 |

The same results are obtained when the test substances of the formulae I and II to XXIV are formulated according to Examples F1 and F3 to F6.

What is claimed is:

1. A herbicidal composition comprising N-[2-(3,3,3-trifluoropropyl)phenylsulfonyl]-N'-(4-methoxy-6-methyl-1,3,5-triazin-2-yl)urea of formula I

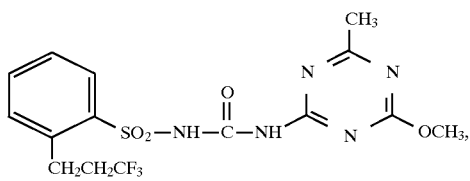

or an agrochemically tolerated salt thereof, and a synergistic amount of a herbicide selected from the group consisting of N-[3-dimethylaminocarbonyl-2-pyridylsulfonyl]-N'(4,6-dimethoxypyrimidin-2-yl)urea of formula X

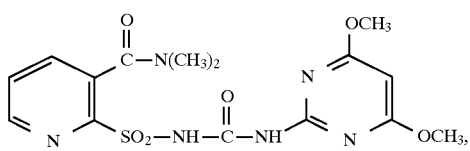

N-[2-(methoxycarbonyl)-3-thiophenylsulfonyl]-N'-(4-methyl-6-methoxy-1,3,5-triazin-2-yl)urea of formula XI

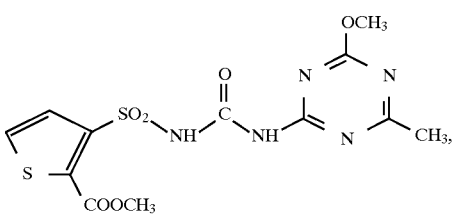

N-[2-(2-chloroethoxy)phenylsulfonyl]-N'-(4-methoxy-6-methyl-1,3,5-triazin-2-yl)urea of formula XIII

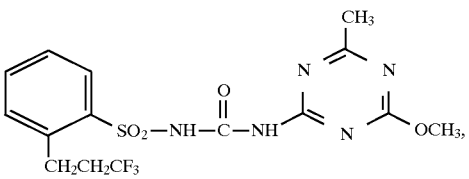

N-[2-(2-methoxyethoxy)phenylsulfonyl]-N'-(4,6-dimethoxy-1,3,5-triazin-2-yl)urea of formula XV

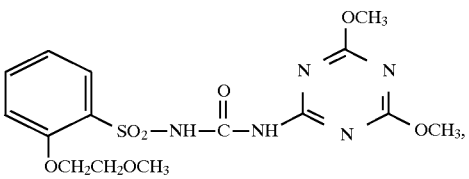

and
N-[2-(methoxycarbonyl)phenylsulfonyl]-N'-(4,6-dimethoxy-pyrimidin-2-yl)urea of formula XVI

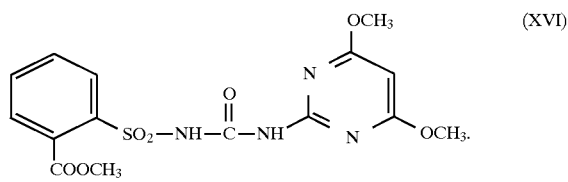

2. A herbicidal composition comprising N-[2-(3,3,3-trifluoropropyl)-phenylsulfonyl]-N'-(4-methoxy-6-methyl-1,3,5-triazin-2-yl)-urea of formula I

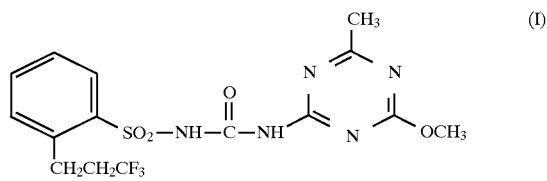

or an agrochemically tolerated salt thereof, and a synergistic amount of

N-[2-(methoxycarbonyl)-phenylsulfonyl]-N'-(4,6-bisdifluoromethoxypyrimidin-2-yl)-urea of formula IV

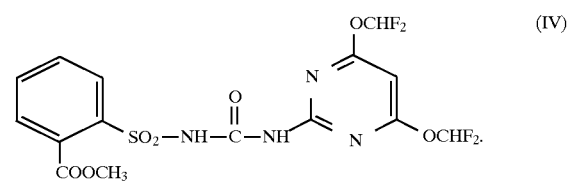

3. A herbicidal composition of claim 2, wherein the mixing ratio of the compound of formula I to the compound of formula IV is 1:0.05 to 1:200.

4. A herbicidal composition of claim 3, wherein the mixing ratio is 1:0.1 to 1:125.

5. A process for controlling undesired plant growth in a crop of useful plants, wherein a herbicidal amount of a composition of claim 2 is allowed to act on the crop plant or the habitat thereof.

6. A process of claim 5, wherein the crop of useful plants is sorghum, cereal, rice, or maize.

7. A process of claim 5, wherein the crop of useful plants is treated with the herbicidal composition at an application rate of 0.01 to 2 kg of active substance per hectare.

8. A process of claim 7, wherein the application rate is 0.02 to 1 kg of active substance per hectare.

9. A herbicidal composition of claim 1, comprising a compound of formula X, XI, or XI.

10. A herbicidal composition of claim 1, comprising a compound of formula XIII.

11. A herbicidal composition of claim 1, comprising a compound of formula XV, XVI or XVI.

12. A herbicidal composition of claim 1, comprising one or two herbicides of formulas X, XI, XIII, XV, XVI, or XVI.

13. A herbicidal composition of claim 1, wherein the mixing ratio of the herbicide of formula I to at least one of the herbicides of formulas X, XI, XII, XV, or XVI is 1:0.05 to 1:200.

14. A herbicidal composition of claim 13, wherein the mixing ratio is 1:0.1 to 1:125.

15. A process for controlling undesired plant growth in a crop of useful plants, wherein a herbicidal amount of a composition of claim 1 is allowed to act on the crop plant or the habitat thereof.

16. A process according to claim 15, wherein the crop of useful plants is sorghum, cereal, rice, or maize.

17. A process according to claim 15, wherein the crop of useful plants is treated with the herbicidal composition at an application rate of 0.01 to 2 kg of active substance per hectare.

18. A process of claim 17, wherein the application rate is 0.02 to 1 kg of active substance per hectare.

* * * * *